(12) United States Patent
Holovacs et al.

(10) Patent No.: US 8,821,496 B2
(45) Date of Patent: Sep. 2, 2014

(54) OSTEOTOMY PROTECTIVE COVER

(75) Inventors: Thomas F. Holovacs, Hingham, MA (US); Daniel J. Williman, Warsaw, IN (US); Conrad L. Klotz, Napanee, IN (US)

(73) Assignee: DePuy Synthes Products, LLC, Raynham, MA (US)

( * ) Notice: Subject to any disclaimer, the term of this patent is extended or adjusted under 35 U.S.C. 154(b) by 1097 days.

(21) Appl. No.: 11/529,885

(22) Filed: Sep. 29, 2006

(65) Prior Publication Data
US 2008/0082175 A1 Apr. 3, 2008

(51) Int. Cl.
*A61B 17/56* (2006.01)
*A61B 17/88* (2006.01)
*A61F 2/46* (2006.01)
*A61B 19/00* (2006.01)
*A61F 2/40* (2006.01)
*A61F 2/30* (2006.01)

(52) U.S. Cl.
CPC ........... *A61F 2/46* (2013.01); *A61F 2250/0004* (2013.01); *A61F 2250/001* (2013.01); *A61B 2019/481* (2013.01); *A61F 2/4014* (2013.01); *A61F 2002/30537* (2013.01); *A61F 2002/30545* (2013.01)
USPC .......................................... 606/86 R; 606/53

(58) Field of Classification Search
USPC ............ 606/70–71, 86 R, 87, 96, 53; 108/17, 108/60, 63, 65, 78, 89, 91–93, 102; 160/211, 214, 218, 222, 223; 220/287
See application file for complete search history.

(56) References Cited

U.S. PATENT DOCUMENTS

| | | | | |
|---|---|---|---|---|
| 1,322,863 A | * | 11/1919 | Bach et al. | 220/287 |
| 1,524,185 A | * | 1/1925 | Lockwood | 220/287 |
| 2,078,211 A | * | 4/1937 | Williams | 220/287 |
| 4,921,120 A | * | 5/1990 | Mizioch | 220/254.2 |
| 5,062,541 A | * | 11/1991 | Galbo | 220/212 |
| 5,147,366 A | * | 9/1992 | Arroyo et al. | 606/94 |
| 5,234,433 A | | 8/1993 | Bert et al. | |
| 5,507,748 A | * | 4/1996 | Sheehan et al. | 606/94 |
| 5,524,407 A | * | 6/1996 | Ricard et al. | 52/473 |
| 5,769,856 A | | 6/1998 | Dong et al. | |
| 5,885,297 A | | 3/1999 | Matsen, III | |
| 6,019,766 A | * | 2/2000 | Ling et al. | 606/94 |
| 6,110,179 A | * | 8/2000 | Flivik et al. | 606/99 |
| 6,127,597 A | | 10/2000 | Beyar et al. | |
| 6,210,423 B1 | | 4/2001 | Kim | |
| 6,284,002 B1 | | 9/2001 | Sotereanos | |
| 6,375,684 B1 | | 4/2002 | Kriek | |
| 6,716,249 B2 | | 4/2004 | Hyde | |

(Continued)

FOREIGN PATENT DOCUMENTS

| | | |
|---|---|---|
| EP | 0 555 004 | 8/1993 |
| EP | 1 402 857 | 3/2004 |
| EP | 1 557 144 | 7/2005 |

*Primary Examiner* — Michael T Schaper
(74) *Attorney, Agent, or Firm* — Maginot, Moore & Beck, LLP

(57) ABSTRACT

A cover for use in protecting a resected surface of a long bone for use in joint arthroplasty is provided. The cover includes a generally planar portion having opposed generally parallel first and second surfaces defining a periphery extending from the first surface and the second surface. The cover also includes a lip extending from the first surface at the periphery of the planar portion in a direction not planar with the generally planar portion.

8 Claims, 21 Drawing Sheets

(56) References Cited

U.S. PATENT DOCUMENTS

| | | |
|---|---|---|
| 7,005,274 B1 | 2/2006 | Terkeltaub et al. |
| 7,337,497 B2 * | 3/2008 | Seidler et al. .................. 16/320 |
| 2003/0212399 A1 * | 11/2003 | Dinh et al. ...................... 606/61 |
| 2005/0027293 A1 * | 2/2005 | LeHuec et al. .................. 606/61 |
| 2005/0149106 A1 * | 7/2005 | DiPoto et al. ................. 606/198 |
| 2005/0273166 A1 * | 12/2005 | Sweeney .................... 623/17.11 |
| 2006/0095042 A1 | 5/2006 | Malkani |

\* cited by examiner

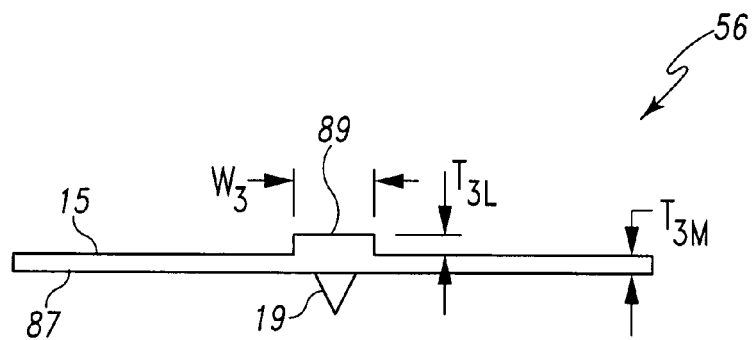
Fig. 17
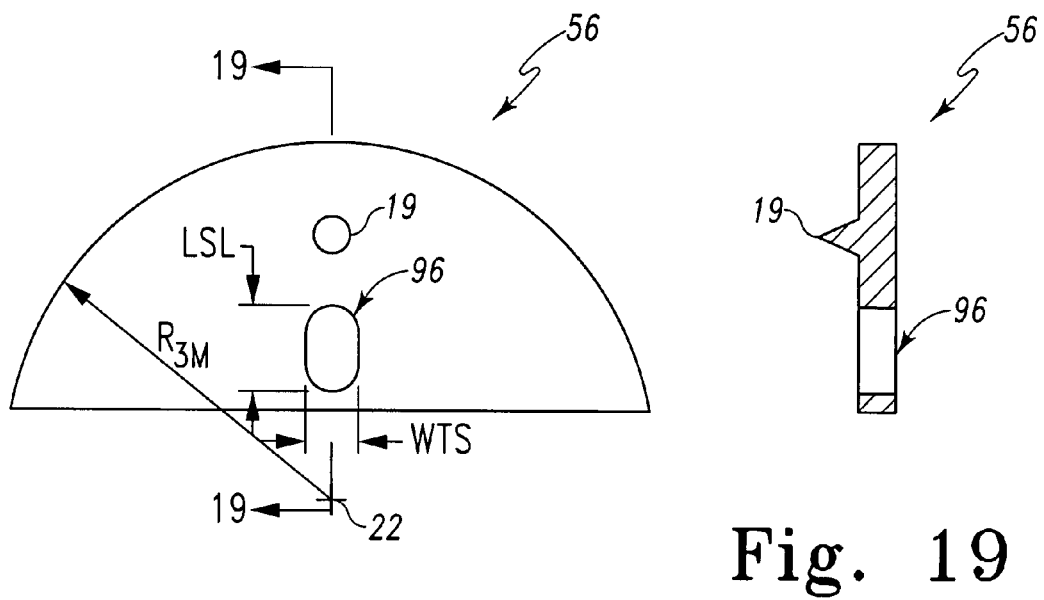
Fig. 18
Fig. 19

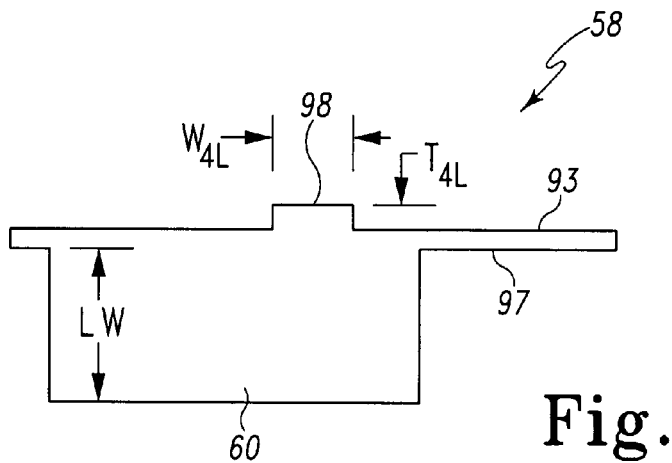
Fig. 20
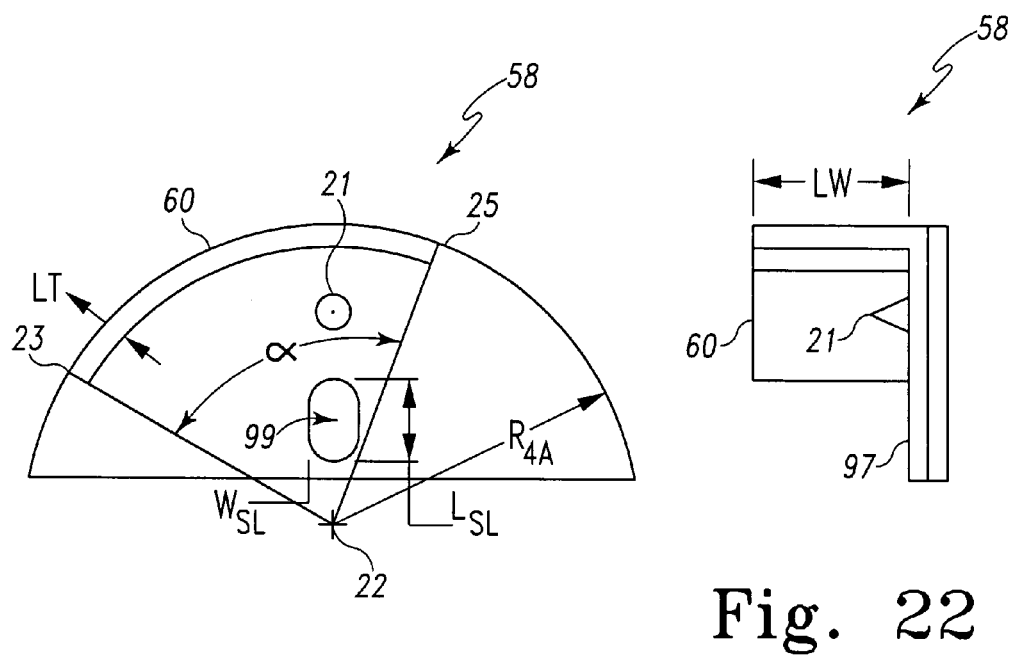
Fig. 21
Fig. 22

OSTEOTOMY PROTECTIVE COVER

TECHNICAL FIELD OF THE INVENTION

The present invention relates generally to the field of orthopaedics, and more particularly, to an instrument for use in arthroplasty.

BACKGROUND OF THE INVENTION

The present invention relates to implantable articles and methods of implanting such articles. More particularly the invention relates to a bone prosthesis, prosthesis trial, instrument and method for implanting the same.

There are known to exist many designs for and methods for implanting implantable articles, such as bone prostheses. Such bone prostheses include components of artificial joints, such as elbows, hips, knees and shoulders.

One such implantable prosthesis is a shoulder prosthesis. During the life time of a patient, it may be necessary to perform a total shoulder replacement procedure on a patient as a result of, for example, disease or trauma, for example disease from osteoarthritis or rheumatoid arthritis. Currently, implantable shoulder prostheses include total shoulder prostheses and humeral head resurfacing replacement, as well as other devices. In a total shoulder replacement procedure, a humeral component having a head portion is utilized to replace the natural head portion of the upper arm bone or humerus. The humeral component typically has an elongated intermedullary stem, which is utilized to secure the humeral component to the patient's humerus. In such a total shoulder replacement procedure, the natural glenoid surface of the scapula is resurfaced or otherwise replaced with a glenoid component that provides a bearing surface for the head portion of the humeral component.

During arthroplasty, for example, a total shoulder replacement arthroplasty, the articulating surface, for example, the humeral head is removed as a first step, leaving an exposed resected surface. The steps in performing humeral joint arthroplasty includes having the surgeon ream the glenoid cavity. If the exposed bone is not well protected while the surgeon reams the glenoid cavity surface, or at other steps in the arthroplasty, the resected humerus may be damaged, resulting in unnecessary bone loss. The use of less invasive surgical procedures reduces the visibility to the resected surface and can lead to increased damage to the resected surface of the bone.

Attempts have been made to protect the resected surface of long bone. For example, osteotomy covers have been provided to be placed on the long bone. The prior art osteotomy protectors are round discs. The use of multiple sizes of the round discs are required to accommodate the wide variety in the size and shape of the resected surface of the long bone.

With only a few fixed round sizes, the surgeon is not able to cover the range of patient size necessary for full protection of the resected long bone. If the fixed sized protector is slightly smaller than the osteotomy surface, the outer cortical bone at the resected surface of the bone may be damaged or loss of bone may occur. If the fixed sized protector is slightly larger than the osteotomy surface, the protector may interfere with soft tissue surrounding the humerus or obstruct the surgeon from the preparing the glenoid. Such obstruction is more pronounced for minimally invasive surgeries where access and view of the surgical sight is more problematic.

The present invention attempts to overcome at least some of the aforementioned problems.

SUMMARY OF THE INVENTION

According to one embodiment of the present invention, a cover for use in protecting a resected surface of a long bone for use in joint arthroplasty is provided. The cover includes a generally planar portion having opposed generally parallel first and second surfaces defining a periphery extending from the first surface and the second surface. The cover also includes a lip extending from the first surface at the periphery of the planar portion in a direction not planar with the generally planar portion.

According to another embodiment of the present invention there is provided a cover for use in protecting a resected surface of a long bone for use in joint arthroplasty. The cover includes a body and a member moveably attached to the body along a first plane. The body and the member define a first periphery of the cover when the body and the member are in a first position with respect to each other and define a second periphery of the cover when the body and the member are in a second position with respect to each other. The second periphery is greater than the first periphery.

According to yet another embodiment of the present invention there is provided an instrument set for use on a long bone in joint arthroplasty. The instrument set includes a cover for use in protecting a resected surface of a long bone. The cover has a body and a member moveably attached to the body along a first plane. The body and the member define a first periphery of the cover when the body and the member are in a first position with respect to each other and define a second periphery of the cover when the body and the member are in a second position with respect to each other. The second periphery is greater than the first periphery. The instrument set also includes a broach for preparing a canal in the long bone.

According to still another embodiment of the present invention there is provided a kit for use on a long bone in joint arthroplasty. The kit includes a cover for use in protecting a resected surface of a long bone. The cover has a body and a member moveably attached to the body along a first plane. The body and the member define a first periphery of the cover when the body and the member are in a first position with respect to each other and define a second periphery of the cover when the body and the member are in a second position with respect to each other. The second periphery is greater than the first periphery. The kit also includes a broach for preparing a canal in the long bone and an implant stem for implantation in to the canal of the long bone.

According to yet another embodiment of the present invention there is provided a method for protecting the resected surface of a long bone for use in joint arthroplasty. The method includes the steps of resecting the long bone and providing a cover including a first portion and a second portion the second portion moveable with respect to the first portion. The method also includes the steps of placing the cover over the resected end of the long bone, adjusting the cover to fit the resected end of the long bone, and securing the cover to the resected end of the long bone.

The cover of the present invention may be used on a resected humerus, but it should be appreciated that such a cover or protector may also be used to protect other long bones, for example a femur. The protector includes a circular body and size adjusting plates that move with respect to the body. For example, four equally spaced size adjustable plates may be used. Each of the four plates can be adjusted outward from the body, increasing the overall size of the protector and providing more coverage of the newly resected exposed bone. The moving plates allow protection of multiple size humeri and varying patient anatomy.

The protector also may include a protective lip extending downwardly from the plate. The lip prevents the surgeon from damaging the humerus while retracting to expose the proximal resected and exposed bone. The adjustable osteotomy protector allows for protection of multiple humeral sizes and varying patient anatomy. The osteotomy protector also provides a protective lip which prevents the surgeon from damaging the humerus to expose the proximal humerus or glenoid while performing the humeral arthroplasty, including exposing the joint articulating surfaces, retracting soft tissue, reaming the humeral canal, and the reaming the glenoid cavity.

The osteotomy cover can be placed on the humerus so that the lip is in position to prevent a surgical retractor or a reamer from damaging the proximal humerus. Also, this osteotomy protector is size adjustable, it can be used for bones of varying sizes, while other systems require multiple covers to account for patients of different anatomies. An adjustable protector also saves room in the instrument cases and saves the surgeon time that would normally be used protecting the resected surface.

For example, according to one aspect of the present invention, a cover for use in protecting a resected surface of a long bone for use in joint arthroplasty is provided. The cover includes a generally planer plane. The body and the member defining a first periphery of the cover when the body and the member a first position with respect to each other and defining a second periphery of the cover when the body and the member are in a second position with respect to each other the second periphery being greater than the first periphery. Thus, the present invention provides for increasing the overall size of the cover.

The technical advantages of the present invention further include the ability to use one cover for varying sizes of anatomies of a resected surface of a long bone. For example, according to another aspect of the present invention, a cover for use in protecting a resected surface of a long bone for use in joint arthroplasty is provided. The cover includes a body and a member moveably attached to the body along a first plane. The moveable member accommodates different size bones. Thus, the present invention provides the ability to use one cover for varying sizes of anatomies of a resected surface of a long bone.

The technical advantages of the present invention include the ability to prevent damage to the long bone, for example, a humerus, to expose the proximal humerus or glenoid while performing the humeral arthroplasty, including exposing the joint articulating surfaces, retracting soft tissue, reaming the humeral canal, and the reaming the gleniod cavity. For example, according to yet another aspect of the present invention, a cover for use in protecting a resected surface of a long bone for use in joint arthroplasty, for example, in shoulder arthroplasty, is provided. The cover includes a generally planer body having opposed generally parallel first and second surfaces defining a periphery extending from the first surface and the second surface. Thus, the present invention provides the ability to prevent damage to the long bone while performing the humeral arthroplasty, including exposing the joint articulating surfaces, retracting soft tissue, reaming the humeral canal, and the reaming the gleniod cavity.

The technical advantages of the present invention further include the ability to reduce inventory and size of instrument cases for joint arthroplasty. For example, according to yet another aspect of the present invention, a cover for use in protecting a resected surface of a long bone for use in joint arthroplasty is provided. The cover includes a body and a member moveable attached to the body along a first plane. The body and the member define a first periphery of the cover when the body and the member are in a first position with respect to each other and define a second periphery of the cover when the body and the member are in a second position with respect to each other. The second periphery is greater than the first periphery. Thus, the present invention provides the ability to reduce inventory and size of instrument cases for joint arthroplasty.

The technical advantages of the present invention further include the ability to save surgery time in finding the proper cover for use in protecting the resected surface of a long bone. For example, according to yet another aspect of the present invention, a cover for use in protecting a resected surface of a long bone for use in joint arthroplasty is provided. The cover includes a body and a member moveable attached to the body along a first plane. The body and the member define a first periphery of the cover when the body and the member are in a first position with respect to each other and a second periphery of the cover when the body and the member are in second position with respect to each other. The second periphery being greater than the first periphery. Thus, the present invention provides for the ability to save surgery time in finding the proper cover for use in protecting the resected surface of a long bone.

The technical advantage of the present invention further include the ability to provide oval and odd shaped covers for resected surfaces for use in joint arthroplasty. For example, according to yet another aspect of the present invention, a cover for use in protecting a resected surface of a long bone for use in joint arthroplasty is provided. The cover includes a body and a member moveably attached to said body along a first plane. The body further includes, for example, a second, and may be a third and fourth member all moveably attachable to the body. If there are four moveable attachable members, the cover may accommodate a greater variety in sizes and shapes of the resected surface of long bones.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which:

FIG. 17 is a plan view of the third member of the protective cover of FIG. 1;

FIG. 18 is a bottom view of the third member of FIG. 17;

FIG. 19 is a cross sectional view of FIG. 18 along the line 19-19 in the direction of the arrows;

FIG. 20 is a plan view of the fourth member of the protective cover of FIG. 1;

FIG. 21 is a bottom view of the fourth member of FIG. 20;

FIG. 22 is another plan view of FIG. 18 of the fourth member of FIG. 20;

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
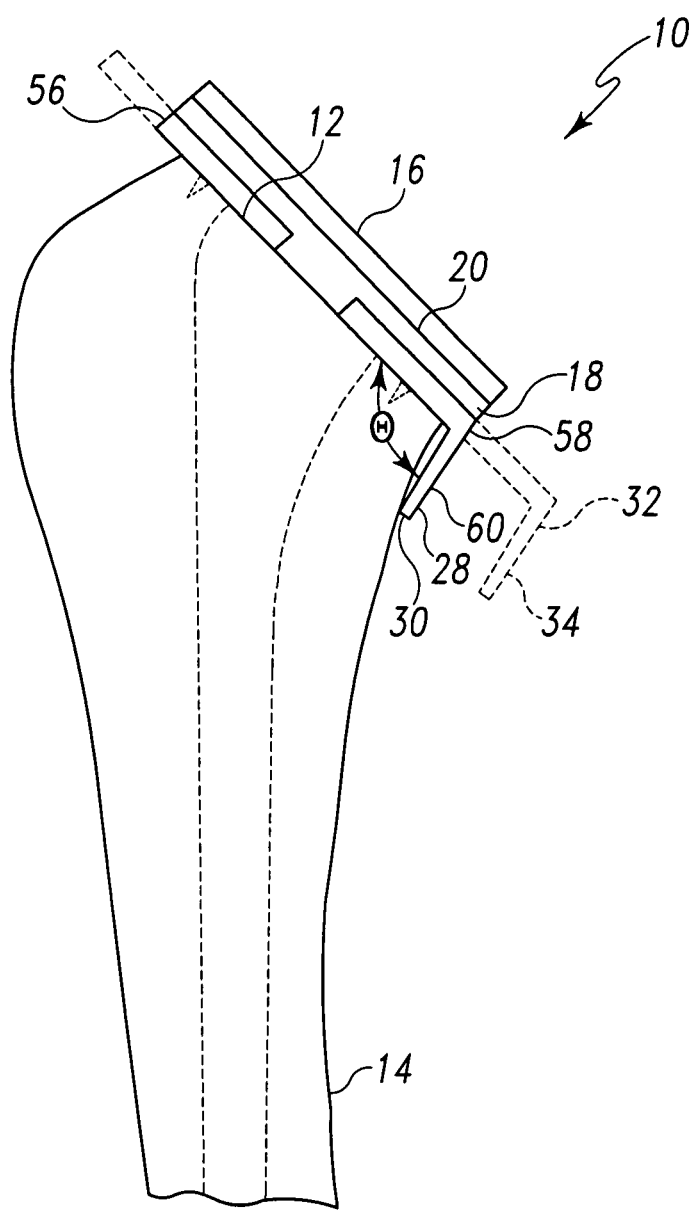
FIG. 1 is a plan view of a protective cover in position on a humerus in accordance with an embodiment of the present invention.

According to the present invention and referring now to FIG. 1, a cover 10 for use in protecting a resected surface 12 of a long bone 14 for use in joint arthroplasty is shown. The long bone 14 as shown in FIG. 1 may be any long bone with a resected surface and may, for example, be in the form of a tibia, a femur, or as is shown in FIG. 1, in the form of a humerus. The cover 10, as is shown in FIG. 1, includes a body 16 and a member 18 moveably attached to the body 16 along a first plane 20. The body 16 and the member 18 define a first periphery 28 of the cover 10 when the body 16 and the member 18 are in a first position 30 with respect to each other. The body 16 and the member 18 define a second periphery 32 of the cover 10 when the body 16 and the member 18 are in a second position 34 with respect to each other, as shown in phantom. The second periphery 34 being greater than the first periphery 28.

Figure 2:
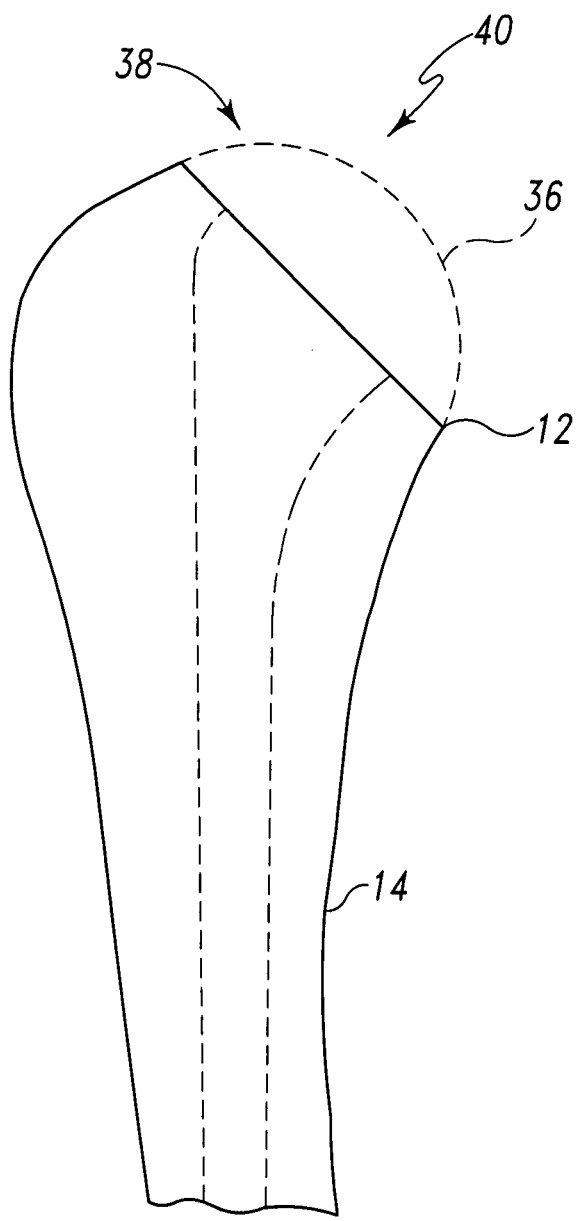
FIG. 2 is a plan view of a resected humerus that may be protected with the protective cover of the present invention.

Referring now to FIG. 2, a long bone 14 in the form as shown in FIG.2 of a humerus is shown in greater detail. The long bone 14, as is shown in FIG. 2, is resected along resected surface 12 with the head 36 of the long bone 14 being removed or resected. The removal of the head 36 exposes intramedullary canal 38, which, as is shown in FIG. 2, may be reamed or drilled or prepared such that a cavity 40 is formed in the long bone 14 to prepare the long bone for receiving the prosthesis 42.

Figure 3:
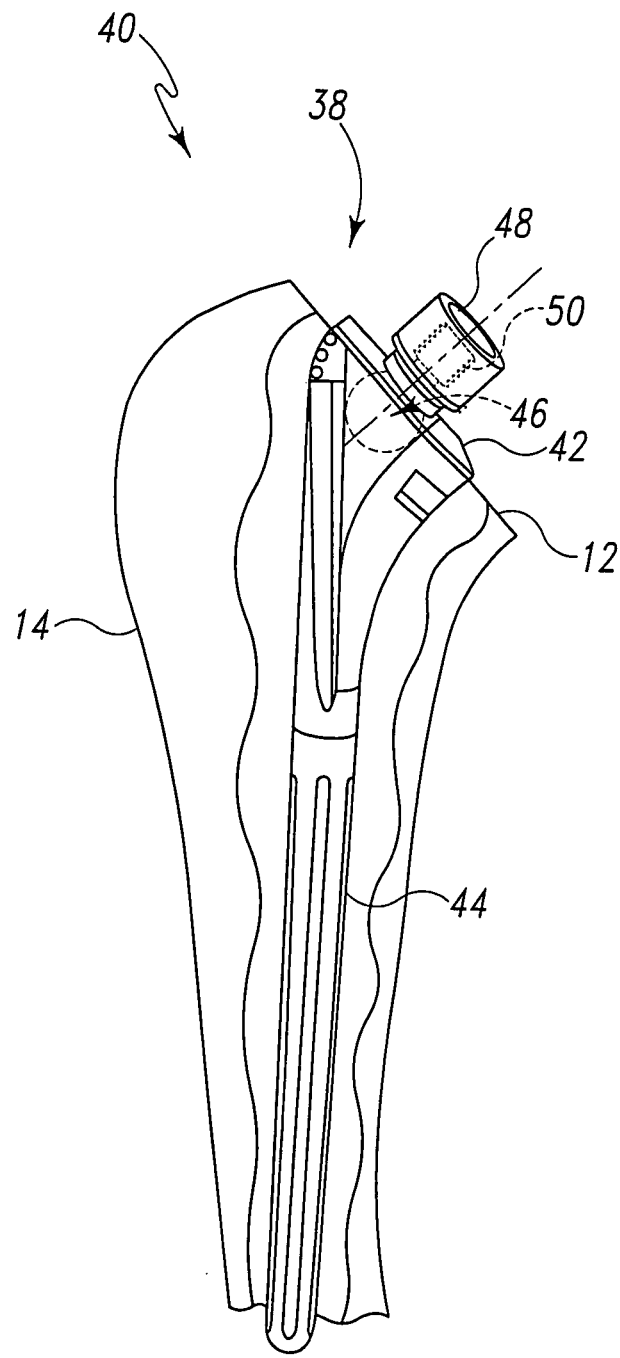
FIG. 3 is a perspective view of a humeral stem assembly that may be inserted into the resected humerus of FIG. 2 that has been protected by the protective cover of the present invention.
Figure 4:
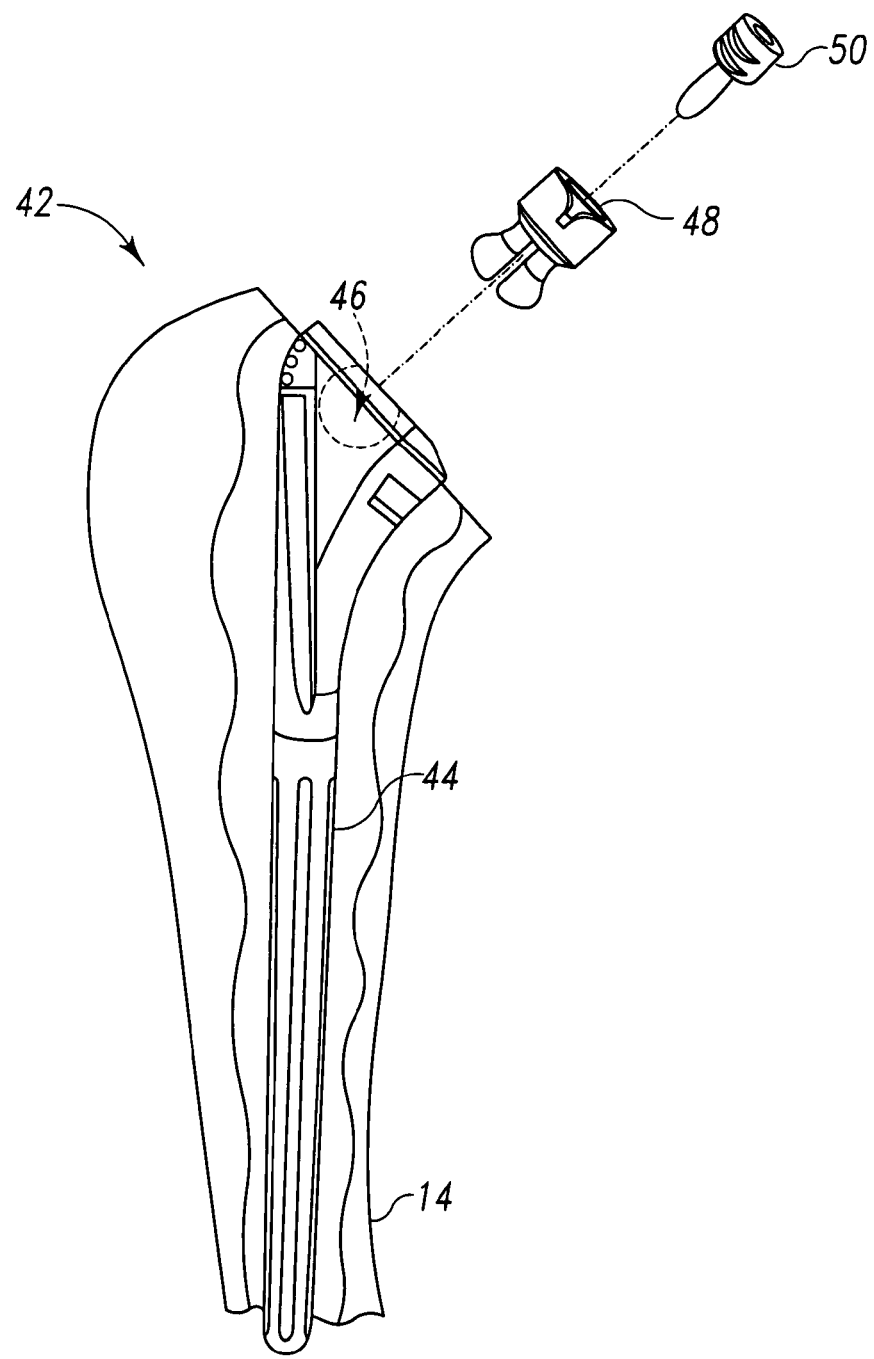
FIG. 4 is an exploded perspective view of a humeral stem assembly of FIG. 3.

Referring now to FIGS. 3 and 4, a trial prosthesis 42 which may be fitted into the cavity 40 formed in intramedullary canal 38 of the long bone 14 is shown. The prosthesis 42, as shown in FIGS. 3 and 4, includes a distal stem 44 which defines a pocket 46 in the proximal part of the distal stem 44. The pocket 46 receives a neck component 48 which is secured to the distal stem 44 by, for example, a fastener 50 in the form of, for example, a screw. A similar implant prosthesis (not shown) may also be placed in canal 38.

Referring now to FIGS. 5-10, the cover 10 is shown in greater detail. While the cover 10 may be provided with two components, the body 16 and the first member 18, it should be appreciated that to provide for a wider variety of shapes and sizes for the cover 10 members in addition to the first member 18 may be included in the cover 10.

Figure 5:
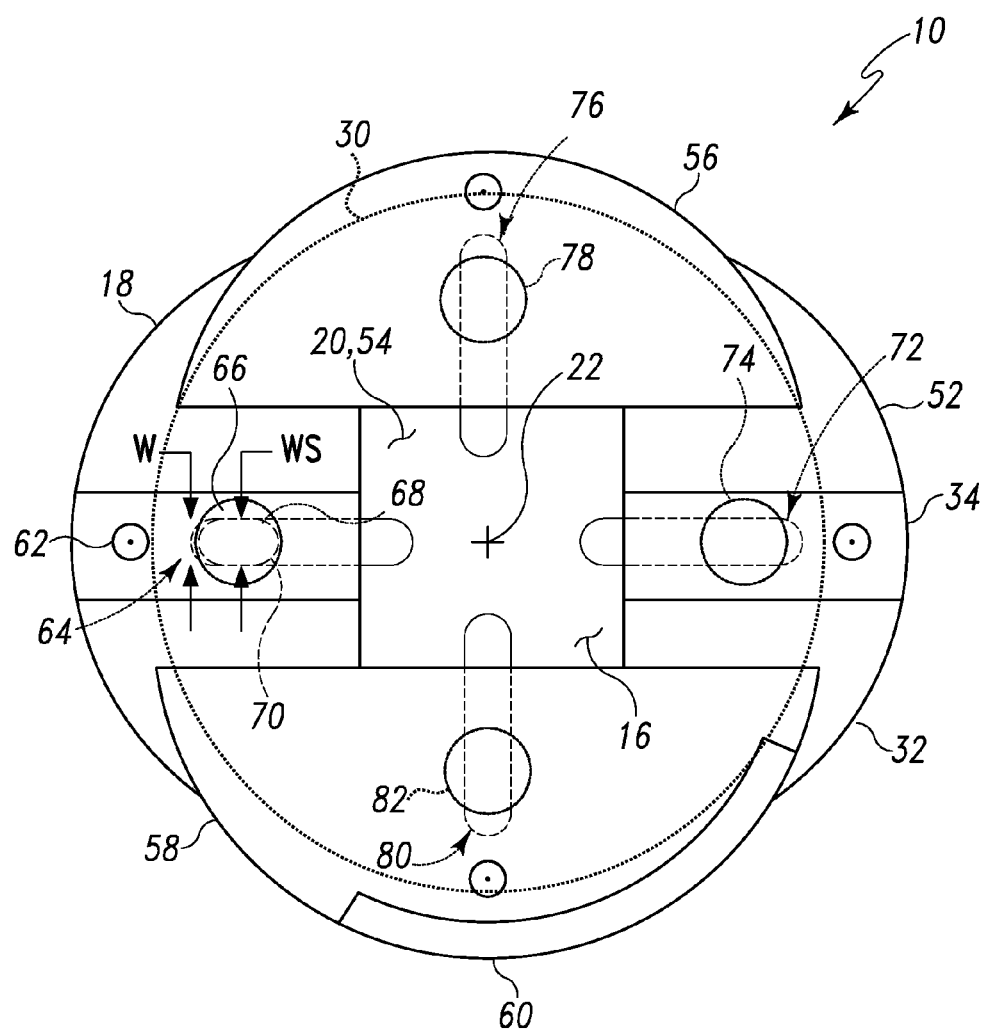
FIG. 5 is a bottom view of the protective cover of FIG. 1 with the moveable members shown in their extended positions.

As shown in FIG. 5, the cover 10 may include a second member 52 which is moveably attached to the body 16 along first plane 20. The first plane 20, as shown in FIG. 5, is in the form or lies along top surface 54 of the body 16. As shown in FIG. 5, the first member 18 slides along the top surface 54 of the body 16 along first plane 20. Similarly, the second member 52 slides in first plane 20 along top surface 54 of the body 16.

The cover 10 may further include a third member 56 which is also slideably attached to the body 16 and may, as is shown in FIG. 5, extend perpendicularly or transversely to the first member 18 and the second member 52. Further, the cover 10 may include a fourth member 58 extending outwardly from the body 16 in a direction opposed to the third member 56. As shown in FIG. 5, the cover 10 may assume first position 30 forming first periphery 28 along dashed lines 30. Similarly, the first member 18, the second member 52, the third member 56, and the fourth member 58 may form second periphery 32 as shown in solid when the cover 10 is in second position 34.

The cover 10 may further include a lip 60 extending from the periphery of the body 16 or from one of the members, for example, the first member 18, the second member 52, the third member 56, or the fourth member 58. As shown in FIG. 5, the lip 60 extends from fourth member 58. The lip 60 may, as shown in FIG. 5, extend from the fourth member 58 in a direction not co-planer with first plane 20. For example and as shown in FIG. 5, the lip may extend perpendicularly or normal to the first plane 20. As shown in FIG. 5, the cover 10 may further include a protrusion, for example, first protrusion 62 extending from first member 18.

While the first periphery 28 and the second periphery 32 may have any suitable shape, it should be appreciated that the cover 10 preferably has a shape to conform to that of the resected surface of the long bone. For example, the cover 10 may have a first periphery 28 and a second periphery 32 that are each arcuate.

It should be appreciated that the sliding members may be connected to the cover 10 in any suitable fashion. For example and as shown in FIG. 5, the body 16 may include a first slot 64 which may extend radially outward from center or origin 22 of the body 16. The first slot 64 may be adapted to receive a first stud 66 which is fixedly secured to first member 18. The first stud 66 may include a head 68 as well as a body 70 having an oval cross section. The body 70 may have a width WS which is matingly fitted to width W of the first slot 64. The stud 66 serves to guide the first member 18 radially inward and outwardly from the origin 22 to position the first member 18 with respect to the body 16, to such a place as is suitable for use with the particular resected surface of the long bone.

Similarly, and as shown in FIG. 5, the body 16 may include a second slot 72 to which a second stud 74 rigidly secured to the second member 52 slideably fits. The second stud 74 is rigidly secured to the second member 52 to permit the second member 52 to move radially outward from origin 22 of the body 16. The body 16 may similarly include a third slot 76 which slideably receives a third stud 78 which is rigidly secured to the third member 56. The third stud 78 is slideably fitted within the third slot 76 to permit the third member 56 to move radially outward from origin 22 of the body 16.

Similarly, the body 16 may similarly include a fourth slot 80 which slideably receives a fourth stud 82 which is rigidly secured to the fourth member 58. The slot 80 serves to permit the fourth member 58 to move radially outward from origin 22 of the body 16.

Figure 6:
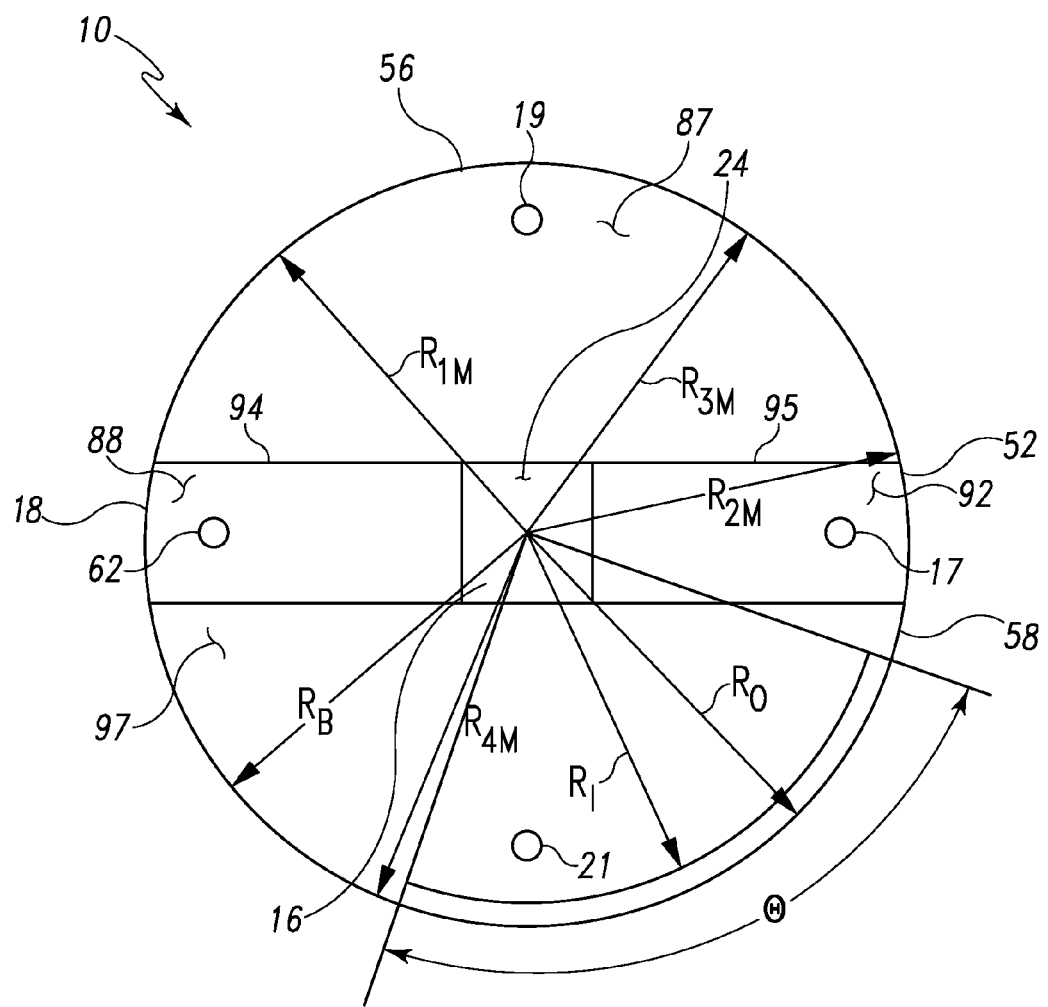
FIG. 6 is a bottom view of the protective cover of FIG. 1 with the moveable members shown in their retracted positions.
Figure 7:
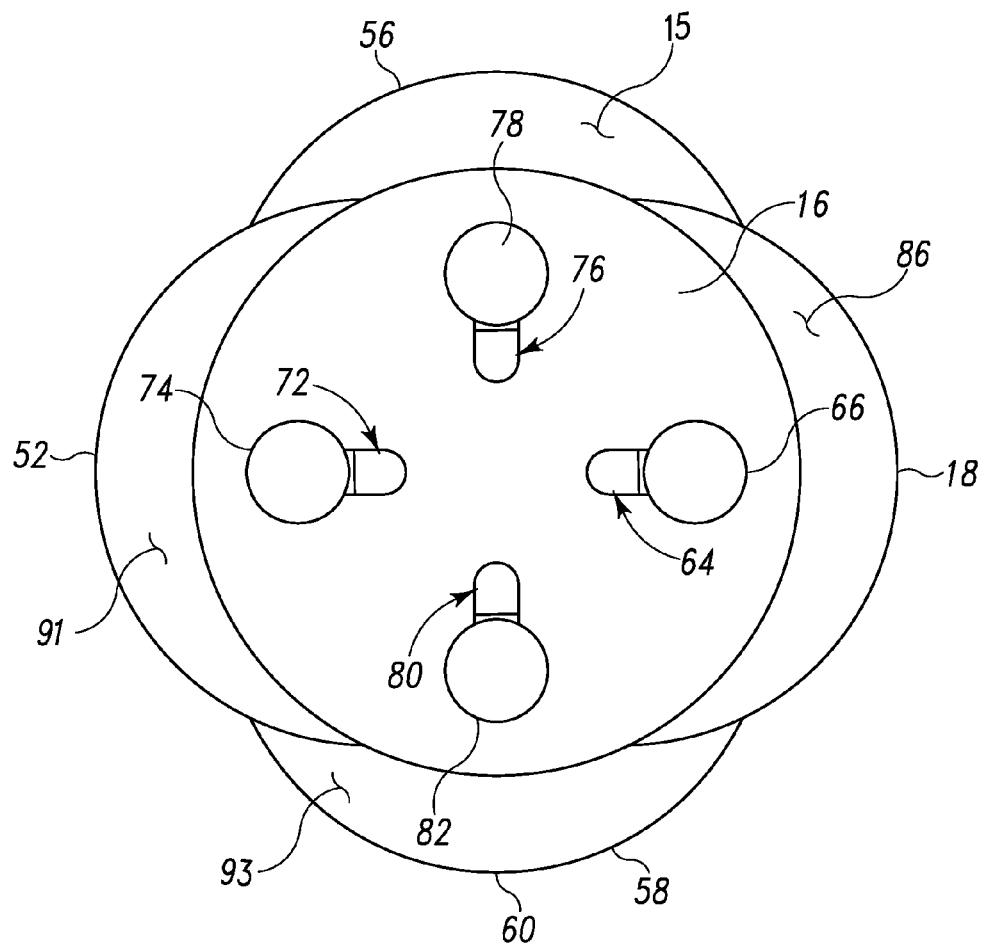
FIG. 7 is a top view of the protective cover of FIG. 1 with the moveable members shown in their extended positions.

Referring now to FIG. 6, the cover 10 is shown with the members 18, 52, 56 and 58 in first position 30. The cover 10, as shown in FIG. 6, includes body 16 as well as first member 18, second member 52, third member 56, and fourth member 58. The first member 18 and the second member 52 slideably fit against the body 16. For example, and as is shown in FIGS. 6 and 7, the body 16 includes an inner face 24 to which outer face 86 of the first member 18 slideably fits. Similarly, the second member 52 includes an outer face 91 which slides along inner face 24 of the body 16.

The third member 56 includes outer face 15 which slides against inner face 88 of the first member 18 and the inner face 92 of the second member 52. Similarly, the fourth member 58 includes an outer face 93 which slideably fits against the inner face 88 of the first member 18 and against the inner face 92 of the second member 52.

The first member 18 includes a land 94 which provides an inner limit to the movement of the third member 56 and the fourth member 58. Similarly, the second member 52 includes a land 95 which serves as an inner movement limit for the third member 56 and the fourth member 58.

While the body 16, the first member 18, the second member 52, the third member 56, and the fourth member 58 may have any suitable shape, preferably the body and members have a periphery that is arcuate, for example, a periphery that is a portion of a circle. For example and as shown in FIG. 6, the periphery of the body 16 is defined by a radius RB extending from origin 22. Similarly, the periphery of the first member 18 is defined by a radius RiM extending from origin 22. The second member periphery is defined by a radius R2M extending from origin 22. Similarly, the third member 56 has a periphery defined by radius R3M extending from origin 22. The fourth member 58 has a periphery defined by radius R4M extending from origin 22.

The lip 60 includes a shape that may be defined as arcuate and may be defined by radius R0 extending from origin 22 and a radius RI extending from origin 22.

Figure 8:
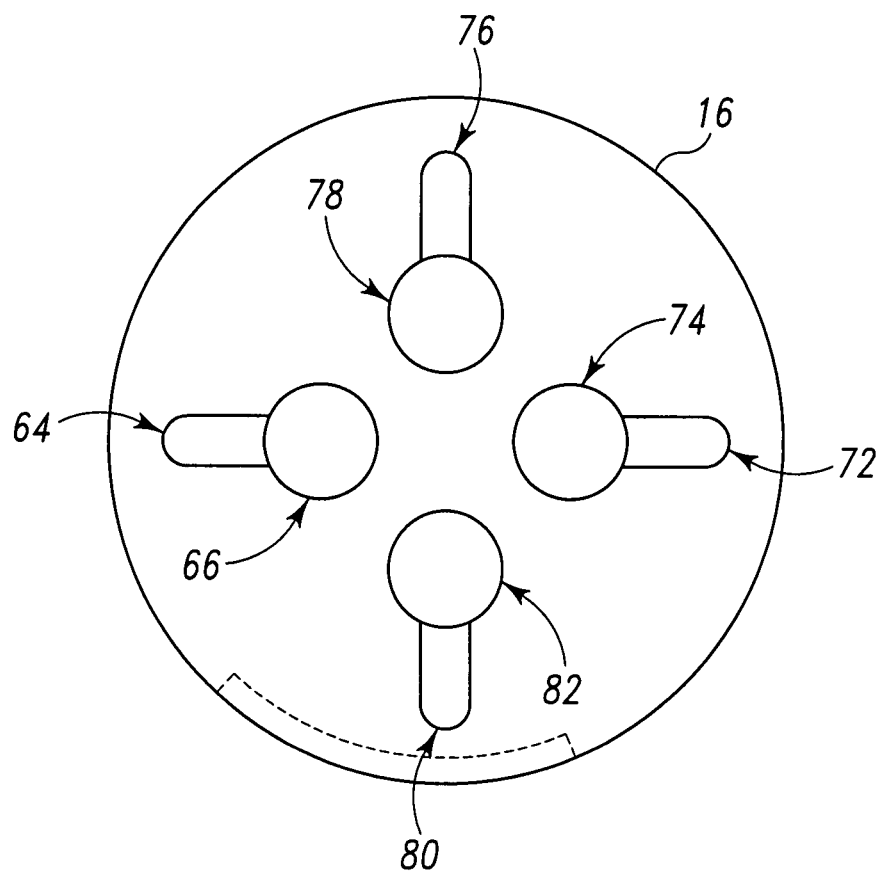
FIG. 8 is a top view of the protective cover of FIG. 1 with the moveable members shown in their retracted positions.

Referring now to FIGS. 7 and 8, the cover 10 is shown with the cover turned 180° with top surface 96 of the body 16 showing on top.

Figure 9:
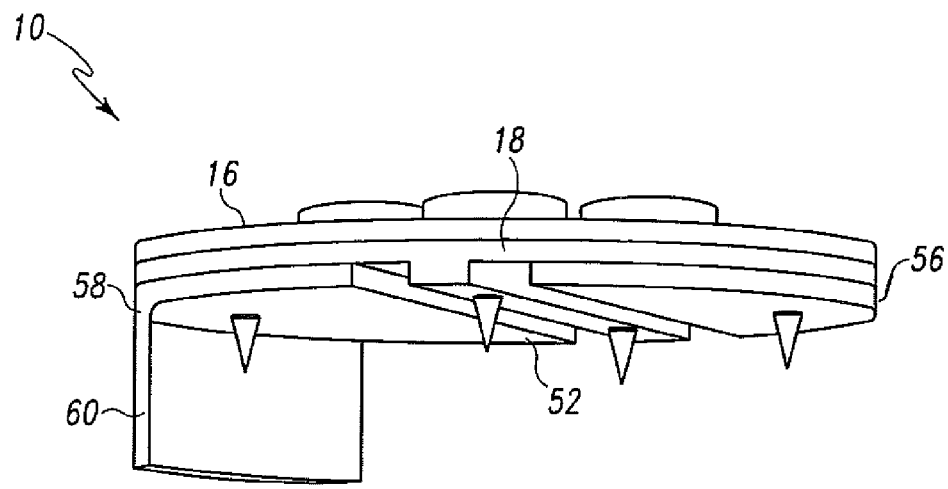
FIG. 9 is a perspective view of the protective cover of FIG. 1.
Figure 10:
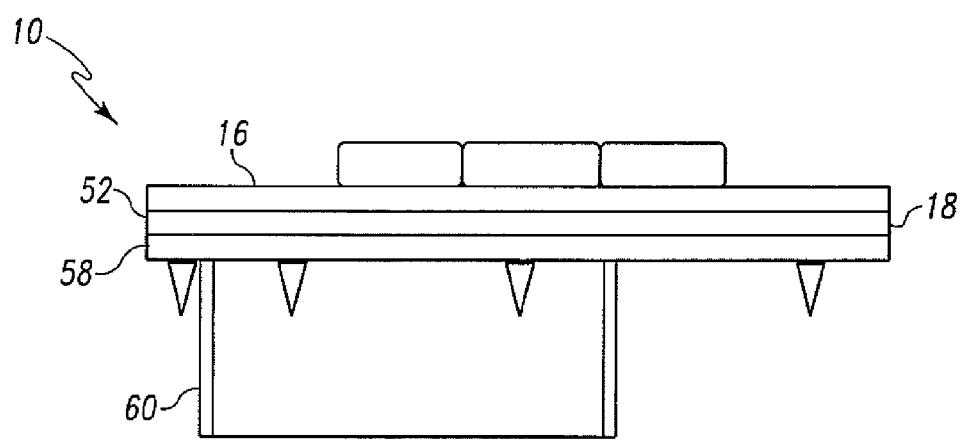
FIG. 10 is another perspective view of the protective cover of FIG. 1.

Referring now to FIGS. 9 and 10, the cover 10 is shown in a perspective view.

Figure 11:
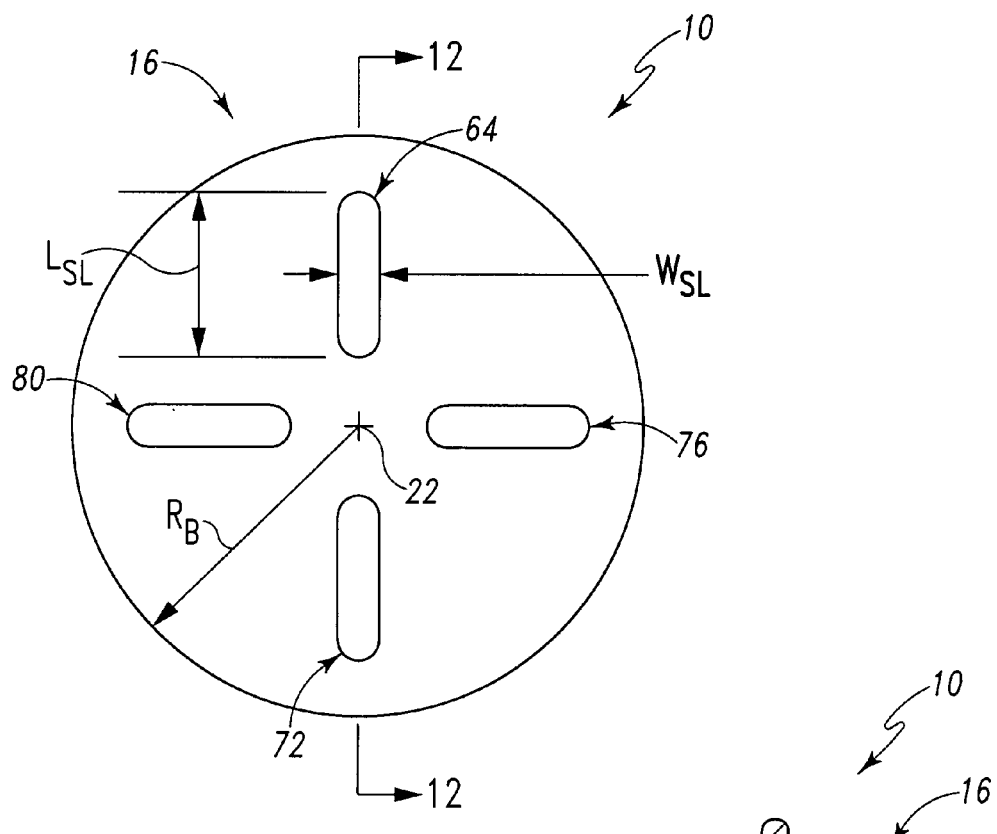
FIG. 11 is a top view of the base of the protective cover of FIG. 1.
Figure 12:
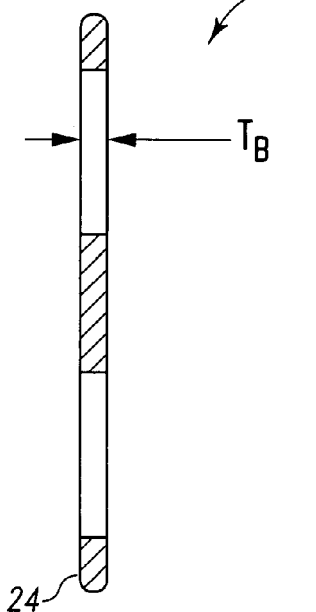
FIG. 12 is a cross sectional view of FIG. 11 along the line 12-12 in the direction of the arrows.

Referring now to FIGS. 11 and 12, the body 16 of the cover 10 is shown in greater detail. The body 16 has a generally cylindrical shape and is defined by radius RB extending from origin 22. The body 16 also has a thickness TB appropriately chosen. The body 16 includes a plurality of slots, each slot having a slot width WSL and a slot length LSL. The width WSL and the length LSL are chosen to mate with the studs, for example, the first stud 66 which should be similar to the second stud 74, the third 78, and the fourth stud 82.

As shown in FIG. 11, the first slot 64 extends radially outward from origin 22. The second slot 72 is opposed to the first slot 64. The third slot 76 and the fourth slot 80 are normal or perpendicular to the first slot 64 and the second slot 72.

Figure 13:
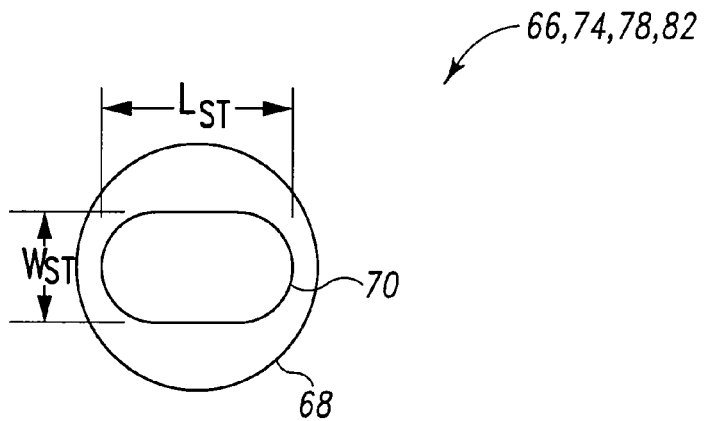
FIG. 13 is a top view of the stud of the protective cover of FIG. 1.
Figure 14:
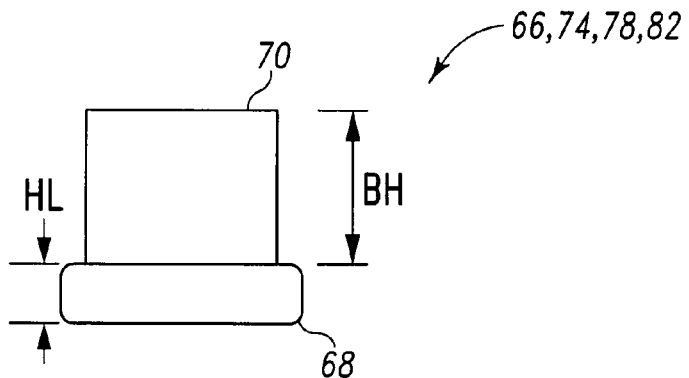
FIG. 14 is a plan view of the stud of FIG. 13.
Figure 15:
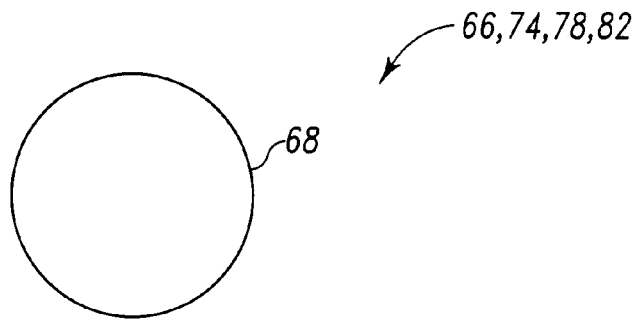
FIG. 15 is a bottom view of the stud of FIG. 13.

Referring now to FIGS. 13, 14 and 15, the studs of the cover 10 of the present invention are shown in greater detail. The first stud 66 is shown in FIGS. 13, 14, and 15. It should be appreciated that the second stud 74, the third 78, and the fourth stud 82 are, for simplicity, identical to the first stud 66. As such, the first stud 66 will be described in FIGS. 13, 14 and 15. The stud 66 includes the head 68 which extends from an end of body 70. The head 38 is cylindrical and is defined by head diameter HD and head thickness HT. The body 70 is defined by a body height BH and is oval defined by a width WST and a length LST. It should be appreciated that the width WST and length LST are selected to matingly fit with the slots 64, 72 76, and 80 of the body 16 of the cover 10.

The studs 66, 74, 78, and 82 may be secured to the respective members 18, 52, 56, and 58 in any suitable fashion. For example, the studs may be interferencely fitted, welded, or threadably secured to the other components of the cover 10.

Figure 16:
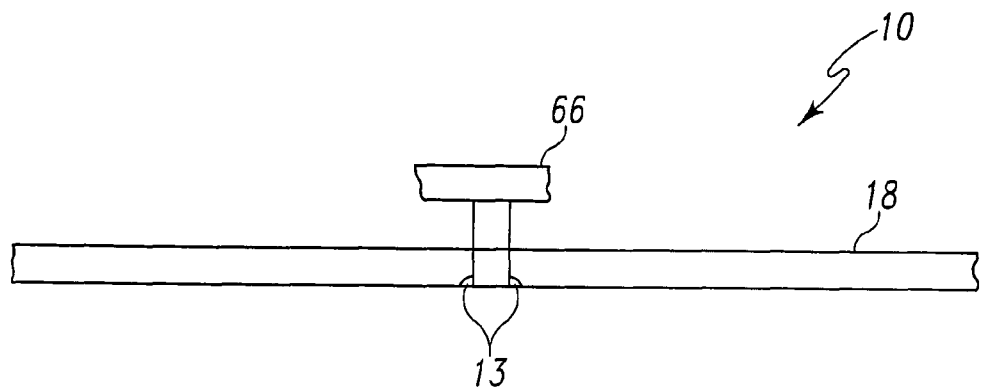
FIG. 16 is a partial view, partially in cross section, of the protective cover of FIG.1 showing the stud in greater detail.

Referring now to FIG. 16, for example the first stud 66 is welded with welding material 13 to first member 18.

Figure 16A:
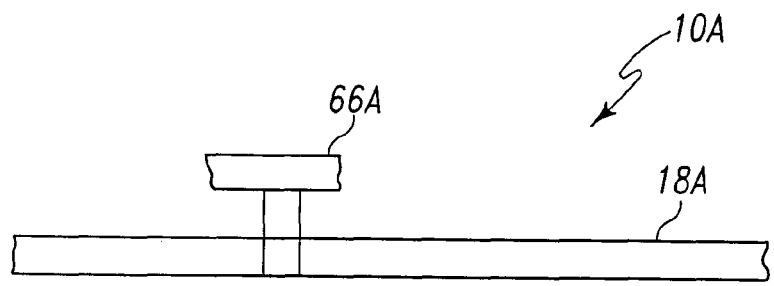
FIG. 16A is a partial view, partially in cross section, of another embodiment of the protective cover of the present invention utilizing a press fitted stud.

Referring now to FIG. 16A, an alternate embodiment of the present invention is shown as cover 10A. The cover 10A includes a stud 66A that is press fitted to first member 18A.

Figure 16B:
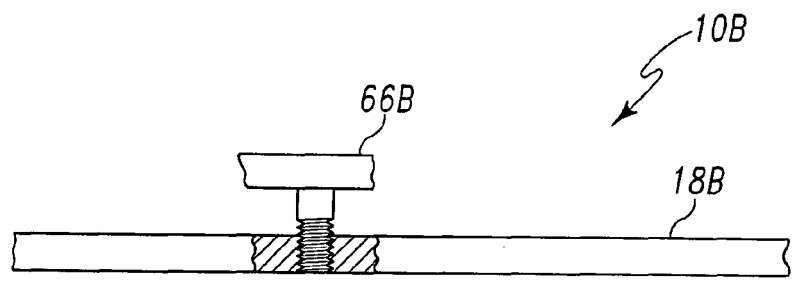
FIG. 16B is a partial view, partially in cross section, of another embodiment of the protective cover of the present invention utilizing a threaded stud.

Referring now to FIG. 16B, another alternate embodiment of the present invention is shown as cover 10B. The cover 10A includes, for example, a first member 18B to which stud 66B is threadably engaged.

Referring now to FIGS. 17, 18, and 19, the third member 56 of the cover 10 is shown in greater detail. The third member 56 has a generally semi-cylindrical shape and has a thickness T3M as well as a radius R3M extending from origin 22. The third member 56 defines the outer face 15 and an opposed parallel inner face 87. The third member further defines a land 89 extending outwardly centrally from outer face 15 and is defined by a thickness T3L and a width W3.

The third member 56 may further include a protrusion 19 extending outwardly from inner face 87 for engagement with the resected face of the long bone 14.

The third member 56 may further include an oblong opening 96 centrally located in the third member 56 and extending from outer face 15 through inner face 87. The oblong opening 96 is adapted to receive the third stud 78 and thus has a width WTS and a length LSL.

Referring now to FIGS. 20, 21, and 22, the fourth member 58 is shown in greater detail. The fourth member 58 has a generally semi-cylindrical shape defined by a thickness T4M and a radius R4M extending from origin 22. The fourth member 58 includes a lip 60 extending outwardly from inner face 97 of the fourth member 58. The inner face 97 and the outer face 93 define a thickness T4M there between. The fourth member 58 further includes a land 98 extending outwardly from outer face 93 and defined by a thickness T4L and a width W4L.

The fourth member 58 further includes an oblong opening 99 centrally located and extending from the inner face 97 to the outer face 93 of the fourth member 58. The oblong opening 99 is defined by, for example, a width WSL and a length LSL corresponding to the dimensions of the fourth stud 82.

The fourth member 58 further includes a protrusion 21 extending inwardly from inner face 97.

Figure 23:
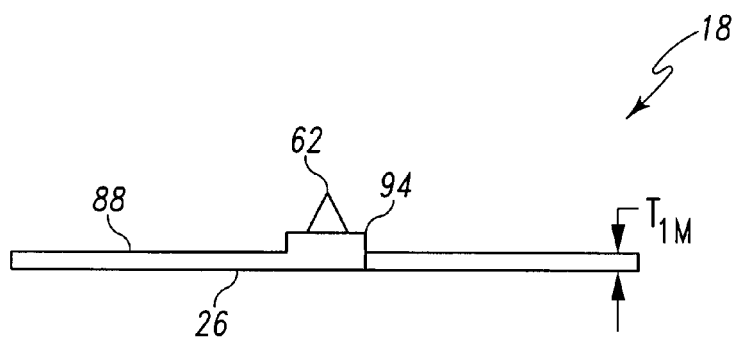
FIG. 23 is a plan view of the first member of the protective cover of FIG. 1.

Referring now to FIGS. 22 and 23, the lip 60 may be defined, for example, by lip width LW and by lip thickness LT. The lip 60 may further be defined by an angle a extending from first end 23 to second end 25 of the lip 60.

Figure 24:
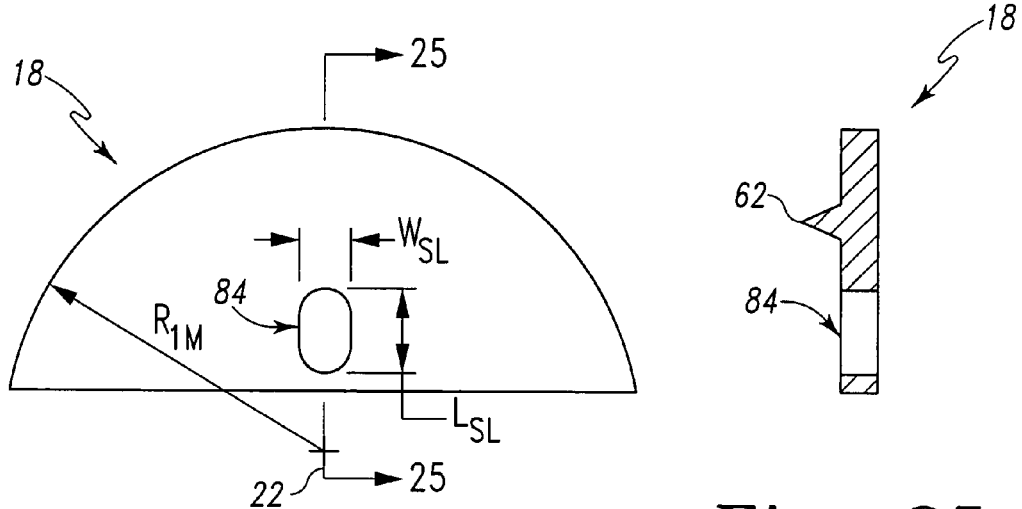
FIG. 24 is a bottom view of the first member of FIG. 23.
Figure 25:
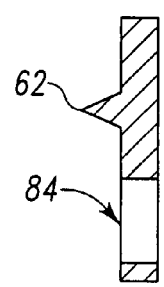
FIG. 25 is a cross sectional view of FIG. 24 along the line 25-25 in the direction of the arrows.

Referring now to FIGS. 23, 24, and 25, the first member 18 is shown in greater detail. It should be appreciated that the first member 18 and the second member 52 may be identical to each other. Thus, FIGS. 23, 24, and 25 are used to describe first member 18, but may also describe the second member 52. The first member 18 may further include a protrusion 62 extending outwardly from inner face 88 for engagement with the resected face of the long bone 14.

The first member 18 has a generally semi-cylindrical shape and is defined by thickness TIM and radius RIM extending from origin 22. The first member 18 includes the inner face 88 and an opposed parallel outer face 26. The land 94 of the first member 18 extends from inner face 88. A first protrusion 62 also extends outwardly from land 94 of the first member 18. The first member 18 further includes a first member oblong opening 84 extending from inner face 88 to outer face 26. The oblong opening 84 has a slot length LSL and a slot width WSL to mate with the dimensions of first stud 66.

Figure 26:
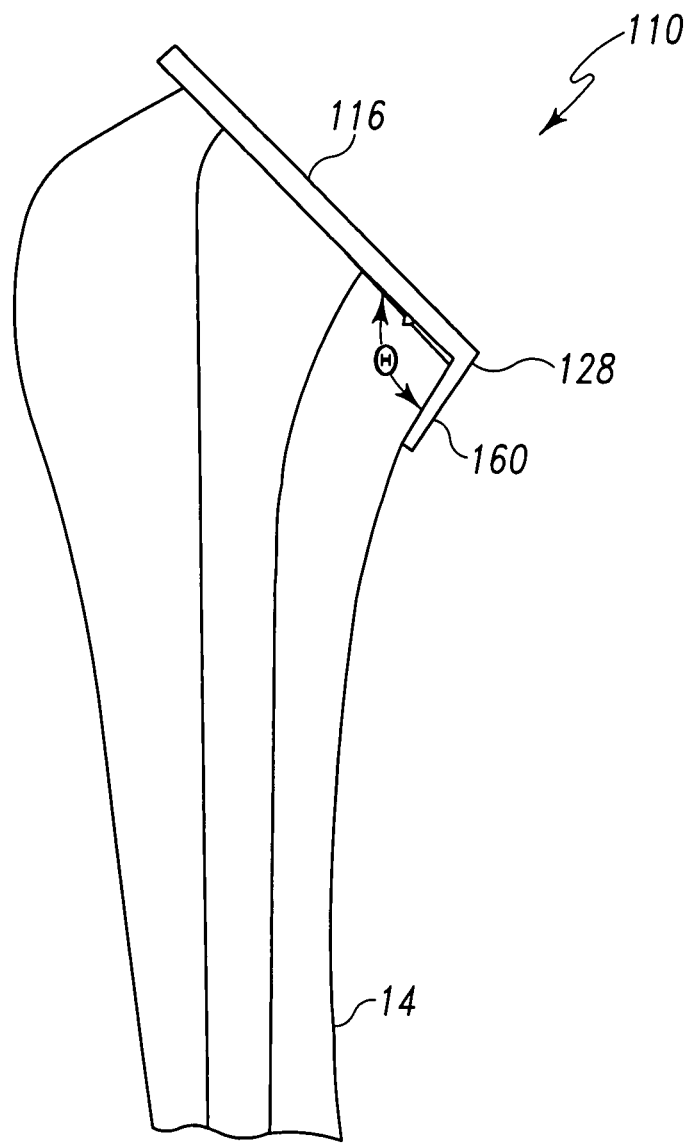
FIG. 26 is a plan view of a one piece protective cover in position on a humerus in accordance with another embodiment of the present invention.

Referring now to FIG. 26, yet another embodiment of the present invention is shown as cover 110. The cover 110 is simpler than the cover 10 of FIGS. 1-25 in that the cover 110 is unitary or made of a one-piece or integral construction. The cover 110 includes a generally cylindrical planer body portion 116 as well as a lip 160 that extends outwardly from periphery 128 of the planer body portion 116.

Figure 27:
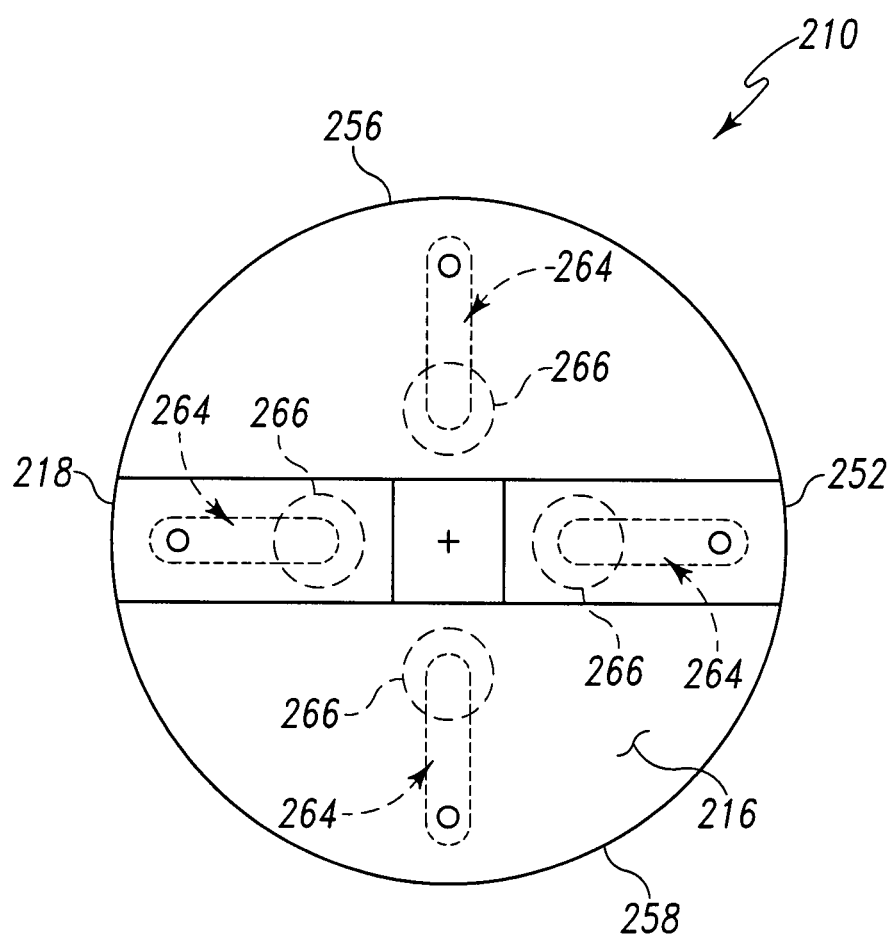
FIG. 27 is a bottom view of a protective cover without a lip in position on a humerus in accordance with yet another embodiment of the present invention.

Referring now to FIG. 27, yet another embodiment of the present invention is shown as cover 210. The cover 210 is very similar to the cover 10 of FIGS. 1-25 except the cover 210 of FIG. 27 does not include a lip. The cover 210 includes a body 216 similar to the body 16 of the cover 10 of FIGS. 1-25. The cover 210 further includes a first member 218 similar to the first member 18 of the cover 10 and a second member 252 similar to the second member 52 of the cover 10 of FIGS. 1-25.

The cover 210 further includes a third member 256 similar to the third member 56 of the cover 10 of FIGS. 1-25 and a fourth member 258 similar to the fourth member 58 of the cover 10 of FIGS. 1-25. The cover 210 further includes slots such as slots 264 similar to slots 64 of the cover 10 and studs 266 which are fitted to the slots 264 to permit the members to mover relative the body 216.

Figure 28:
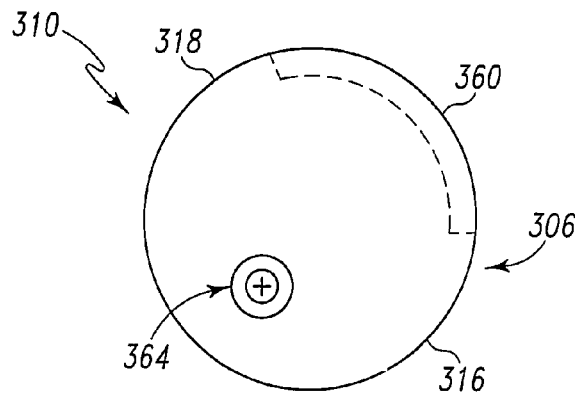
FIG. 28 is a bottom view of a three piece protective cover in a contracted position in accordance with another embodiment of the present invention.
Figure 29:
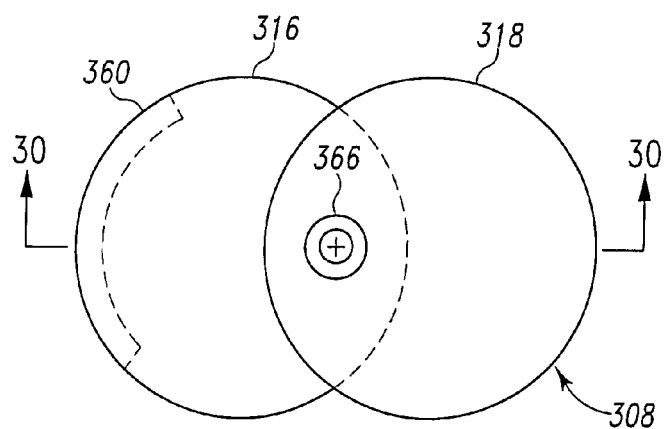
FIG. 29 is a bottom view of the three piece protective cover of FIG. 28 in an expanded position.
Figure 30:
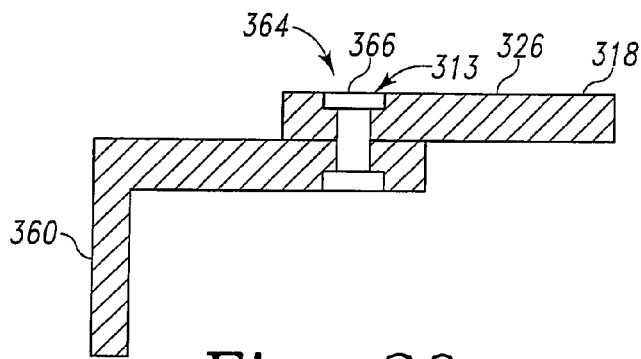
FIG. 30 is a cross sectional view of FIG. 29 along the line 30-30 in the direction of the arrows.

Referring now to FIGS. 28, 29 and 30, yet another embodiment of the present invention is shown as cover 310. The cover 310 is quite simple and includes only three pieces. The cover 310 includes a body 316 having a generally circular disc shape and an opening 364 positioned off-center on the body 316. The cover 310 further includes a first member 318 which has a cylindrical disc shape similar to that of the body 316 and a stud 366 is rigidly secured off-center by welding material 313 from first face 326 of the first member 318. The stud 366 is pivotally secured to the opening 364 in the body 316 to rotatably secure the first member 318 to the body 316 to form the cover 310. The cover 310 may further include the lip 360 which may be secured to the body 316 and extend in a direction opposed to that of the first member 318.

Referring now to FIGS. 28 and 29, the cover 310 is in a first position 306 as shown in FIG. 28 when the first member 318 and the body 316 are in alignment with each other. As shown in FIG. 29, the cover 310 is in a second position 308 when the first member 318 is out of alignment with the body 316.

Figure 31:
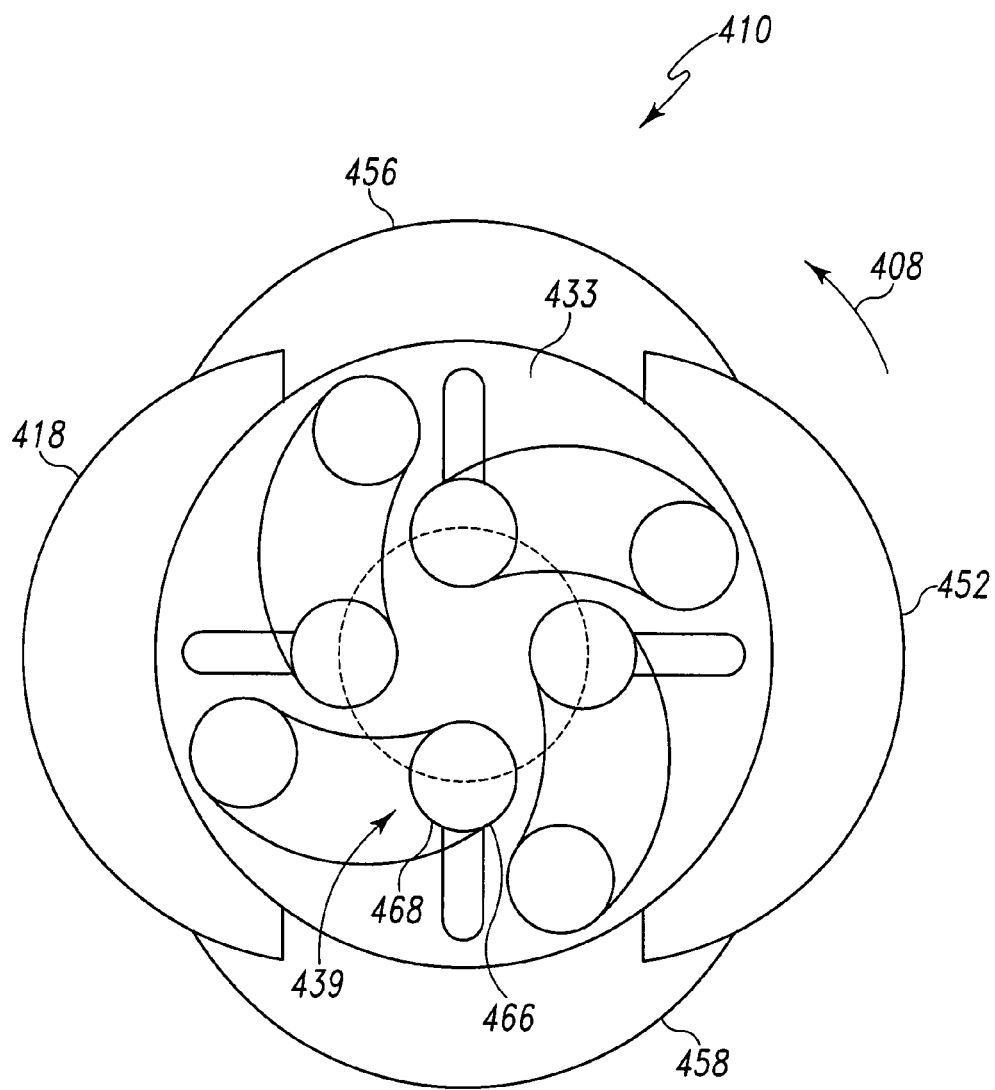
FIG. 31 is a bottom view of a protective cover with a spiral guide plate in accordance with another embodiment of the present invention.
Figure 32:
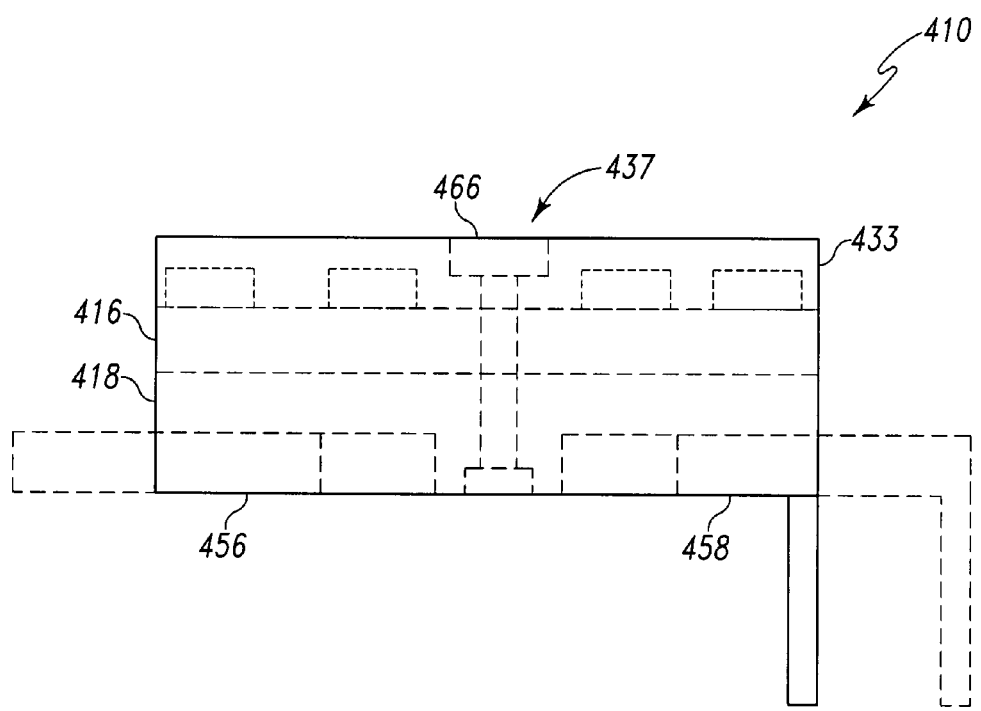
FIG. 32 is plan view of FIG. 31, partially in cross section.

Referring now to FIGS. 31 and 32, yet another embodiment of the present invention is shown as cover 410. The cover 410 is similar to the cover 10 of FIGS. 1-25 except that the cover 410 includes an additional component in the form of an actuator 433 which is positioned against body 416 and may be rotatably secured to the body 416 by a stud 435 that is rigidly secured to the body 416 and rotatably secured through opening 437 formed in the actuator 433. The actuator 433 may include arcuate slots 439 which slideably receive the heads 468 of the studs 466 such that as the actuator 433 is rotated in the direction of arrow 408, the studs 466 are forced outwardly thereby forcing the members 418, 452, 456, and 458 outwardly in a similar fashion to provide a simple and quick method of actuating and adjusting the cover 410.

Figure 33:
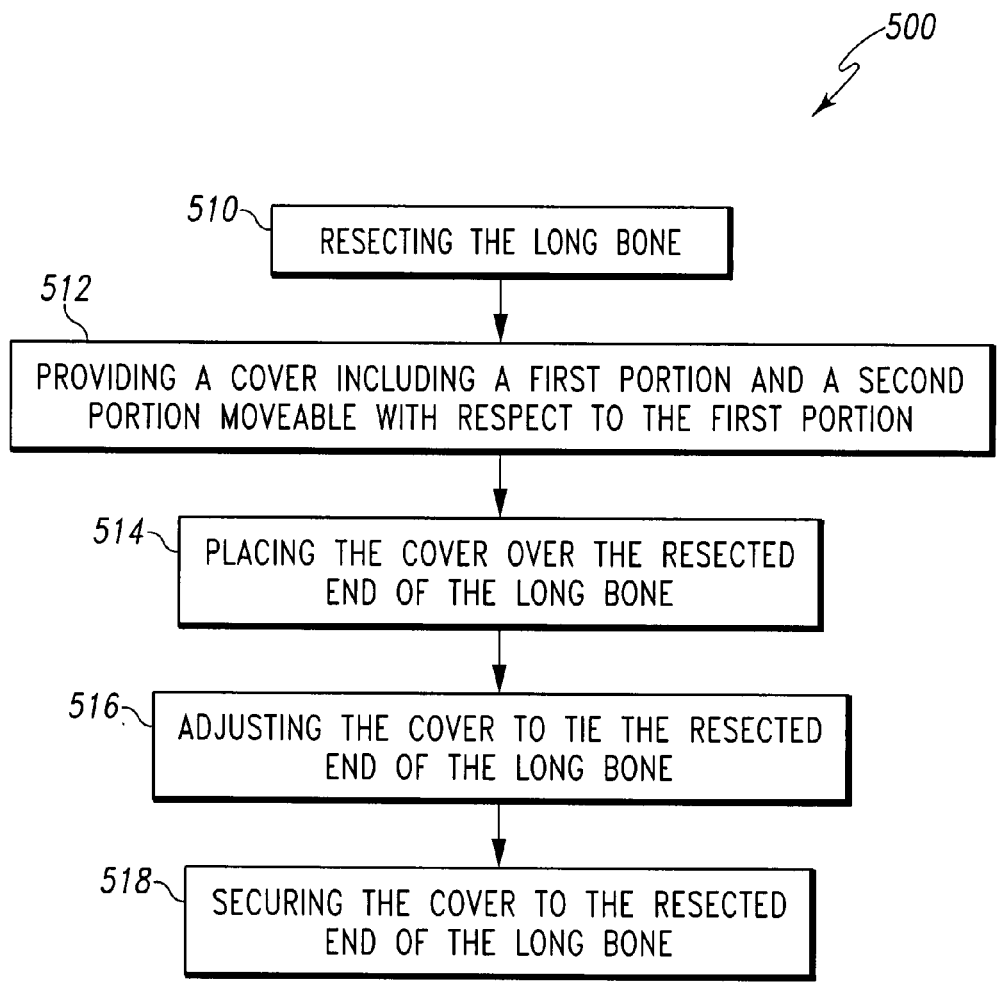
FIG. 33 is a flow chart of a method for performing shoulder arthroplasty in accordance with another embodiment of the present invention.

Referring now to FIG. 33, yet another embodiment of the present invention is shown as surgical procedure or method 500. The method includes a first step 510 of resecting the long bone and a second step 512 of providing a cover including a first portion and a second portion the second portion moveable with respect to the first portion. The method also includes a third step 514 of placing the cover over the resected end of the long bone and a fourth step 516 of adjusting the cover to fit the resected end of the long bone. The method also includes a fifth step 518 of securing the cover to the resected end of the long bone.

Although the present invention and its advantages have been described in detail, it should be understood that various changes, substitutions, and alterations can be made therein without departing from the spirit and scope of the present invention as definite by the appended claims.

We claim:

1. A cover for use in protecting a resected surface of a long bone, comprising:
   a body extending along a first plane and including a first surface;
   a first member attached to the body and movable with respect to the body generally along a second plane parallel to the first plane between a first position and a second position, the first member including (i) a second surface in opposition to the first surface and (ii) a third surface;
   a second member attached to the body and movable with respect to the body generally along the second plane between a first position and a second position, the second member including (i) a fourth surface in opposition to the first surface and (ii) a fifth surface; and
   a third member attached to the body and movable with respect to the body generally along a third plane parallel to the first plane between a first position and a second position, the third member including a sixth surface in opposition to the third surface and the fifth surface, wherein when each of the first member, the second member, and the third member is in its respective first position, the body and each of the first member, the second member, and the third member define a first periphery which, when projected onto the first plane, encompasses a first area, when each of the first member, the second member, and the third member is in its respective second position, the body and each of the first member, the second member, and the third member define a second periphery which, when projected onto the first plane, encompasses a second area, and the second area encompasses the first area.

2. The cover of claim 1, wherein:

the first member and the body form a continuous barrier along the first plane within the first periphery when the first member is in its first position; and the first member and the body form a substantially continuous barrier along the first plane within the second periphery when the first member is in its second position.

3. The cover of claim 2, further comprising a lip extending from a periphery of one of the body and the first member in a direction away from the first plane.

4. The cover of claim 3, wherein the lip extends generally normal to the first plane.

5. The cover of claim 2, wherein a periphery of one of said body and said first member is arcuate when projected onto the first plane.

6. The cover of claim 2 wherein the body defines a first internal wall defining a first slot and a second internal wall defining a second slot, the cover further comprising:

a first guide connected to the first member, the first guide slideably fitted to the first slot; and a second guide connected to the second member, the second guide slideably fitted to the second slot.

7. The cover of claim 6:

wherein the first slot defines a first longitudinal axis and the second slot defines a second longitudinal axis, the first longitudinal axis and the second longitudinal axis being collinear.

8. The cover of claim 7 wherein the body defines a third internal wall defining a third slot and a fourth internal wall defining a fourth slot, the cover further comprising:

a fourth member attached to the body and movable with respect to the body along the first plane, the fourth member opposed to the third member;

a third guide connected to the third member, the third guide slideably fitted to the third slot; and a fourth guide connected to the fourth member, the fourth guide slideably fitted to the fourth slot.

* * * * *